US006015708A

United States Patent [19]
Sherwin et al.

[11] Patent Number: 6,015,708
[45] Date of Patent: *Jan. 18, 2000

[54] GENE MANIPULATION AND EXPRESSION USING GENOMIC ELEMENTS

[75] Inventors: Stephen Sherwin, San Francisco; Sue Klapholz, Stanford, both of Calif.; Arthur Skoultchi, Larchmont, N.Y.

[73] Assignee: Cell Genesys, Inc., Foster City, Calif.

[ * ] Notice: This patent is subject to a terminal disclaimer.

[21] Appl. No.: 08/462,947

[22] Filed: Jun. 5, 1995

Related U.S. Application Data

[63] Continuation of application No. 08/102,567, Aug. 5, 1993, Pat. No. 5,578,461, which is a continuation of application No. 08/001,898, Jan. 7, 1993, abandoned, which is a continuation of application No. 07/696,216, May 6, 1991, abandoned, which is a continuation-in-part of application No. 07/432,069, Nov. 6, 1989, abandoned.

[30] Foreign Application Priority Data

Nov. 6, 1990 [WO] WIPO ............... PCT/US90/06425

[51] Int. Cl.⁷ ............... C12N 1/19; C12N 5/10; C12N 15/81; C12N 15/85
[52] U.S. Cl. ............... 435/325; 435/254.21; 435/320.1; 435/70.1; 435/455; 435/471
[58] Field of Search ............... 435/172.3, 320.1, 435/254.21, 471, 70.1, 325, 455; 536/23.1

[56] References Cited

U.S. PATENT DOCUMENTS

| | | | |
|---|---|---|---|
| 4,656,134 | 4/1987 | Ringold | 435/91 |
| 4,740,461 | 4/1988 | Kaufman | 435/69.1 |
| 5,272,071 | 12/1993 | Chappel | 435/6 |
| 5,578,461 | 11/1996 | Sherwin et al. | 435/69.1 |

FOREIGN PATENT DOCUMENTS

| | | |
|---|---|---|
| 2646438 | 3/1989 | France . |
| WO 90/11354 | 10/1990 | WIPO . |
| WO 91/09955 | 7/1991 | WIPO . |

OTHER PUBLICATIONS

Mansour et al., 1988, "Disruption of the Proto–Oncogene int–2 in Mouse Embryo–Derived Stem Cells: A General Strategy for Targeting Mutations to Non–Selectable Genes", Nature 336:348–352.

Weidle et al., 1988, "Amplified Expression Contructs for Human Tissue–Type Plasminogen Activitor in Chinese Hamster Ovary Cells: Instability in the Absence of Selective Pressure", Gene 66:193–203.

Murnane and Yezzi, 1988, "Association of High Rate of Recombination with Amplification of Dominant Selectable Gene in Human Cells", Somatic Cell and Mol. Genet. 14:273–286.

Thomas and Capecchi, 1987, "Site–Directed Mutagenesis by Gene Targeting in Mouse Embryo–Derived Stem Cells" Cell 51:503–512.

Song et al., 1987, "Accurate Modification of a Chromosomal Plasmid by Homologous Recombination in Human Cells", Proc. Natl. Acad. Sci. USA 84:6820–6824.

Liskay et al., 1984, "Homologous Recombination Between Repeated Chromosomal Sequences in Mouse Cells", C.S.H.Q.B. 49:183–189.

Rubnitz and Subramani, 1984, "The Minimum Amount of Homology Required for Homologous Recombination in Mammalian Cells", Mol. Cell. Biol. 4:2253–2258.

Kim and Smithies, 1988, "Recombinant Fragment Assay for Gene Targeting Based on the Polymerase Chain Reaction", Nucl. Acids Res. 16:8887–8903.

Burke et al., 1987, "Cloning of Large Segments of Exogenous DNA into Yeast by Means of Artificial Chromosome Vectors", Science 236:806–812.

Garza et al., 1989, "Mapping the *Drosophila* Genome with Yeast Artificial Chromosomes" Science 246:641–646.

Brownstein et al., 1989, "Isolation of Single–Copy Human Genes from a Library of Yeast Artifical Chromosome Clones", Science 244:1348–1351.

Traver et al., 1989, "Rapid Screening of a Human Genomic Library in Yeast Artificial Chromosomes for Single–Copy Sequences", Proc. Natl. Acad. Sci. USA 86:5898–5902.

Botstein et al., 1988, "Yeast: An Experimental Organism for Modern Biology", Science 240:1439–1443.

Smith et al., 1990, "Amplification of Large Artificial Chromosomes", Proc. Natl. Acad. Sci. USA 87:8242–8246.

Pachnis et al., 1990, "Transfer of a Yeast Artificial Chromosome Carrying Human DNA from *Saccharomyces cerevisiae* into Mammalian Cells", Proc. Natl. Acad. Sci. USA 87:5109–5113.

Pavan et al., 1990, "Modification and Transfer into an Embryonal Carcinoma Cell Line of a 360–Kilobase Human–Derived Yeast Artificial Chromosome", Mol. Cell. Biol. 10:4163–4169.

D'Urso et al., 1990, "Human Glucose–6–Phosphate Dehydrogenase Gene Carried on a Yeast Artificial Chromosome Encodes Active Enzyme in Monkey Cells", Genomics 7:531–534.

(List continued on next page.)

*Primary Examiner*—Scott D. Priebe
*Attorney, Agent, or Firm*—Pennie & Edmonds LLP

[57] ABSTRACT

Expression of mammalian target genes is achieved by employing chromosomal target DNA, either native primary cells or YACs in a yeast host, where the YACs include a fragment of a mammalian chromosome, the fragment comprising the target gene. Employing homologous recombination, an amplifiable gene is integrated into the mammalian fragment at a site to allow for amplification. In the same step, or one or more steps, as desired, the mammalian gene and/or the transcriptional system may be modified by in vivo mutagenesis. The resulting construct from homologous recombination may then be transformed into a mammalian expression host and integrated into the host genome, either randomly or by homologous recombination. The amplifiable gene may then be amplified by an appropriate agent providing for multiple copies of the target gene and the expression host grown to provide for high yields of the desired wild-type or modified protein.

21 Claims, No Drawings

OTHER PUBLICATIONS

Elceiri et al., 1991, "Stable Integration and Expression in Mouse Cells of Yeast Artificial Chromosome Harboring Human Genes", Proc. Natl. Acad. Sci. USA 88:2179–2183.

Huxley et al., 1991, "The Human HPRT Gene on a Yeast Artificial Chromosome is Functional When Transferred to Mouse Cells by Cell Fusion", Genomics 9:742–750.

Perucho et al., 1980, "Genetic and Physcial Linkage of Exogenous Sequences in Transferred Cells", Cell 22:309–317.

Allshire et al., 1987, "A Fission Yeast Chromosome Can Replicate Autonomously in Mouse Cells", Cell 50:391–403.

Paven et al., 1990, "Generation of Deletion Derivatives by Targeted Transformation of Human–Derived Yeast Artificial Chromosomes", Proc. Natl. Acad. Sci. USA 87:1300–1304.

Thompson et al., 1989, "Germ Line Transmission and Expression of a Corrected HPRT Gene Produced by Gene Targeting in Embryonic Stern Cells", Cell 56:313–321.

```
                          SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
           (A) LENGTH: 34 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:1:

GAATTCAGAT CTGCAGTTAC TGAGAACTCA TAAG                                    34

(2) INFORMATION FOR SEQ ID NO:2:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:2:

GAATTCGGGC CCTGCAGTGG AACAAGCTTA ATG                                     33

(2) INFORMATION FOR SEQ ID NO:3:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: DNA (xi) SEQUENCE DESCRIPTION: SEQ ID NO:3:

GGTCGACCTG GATCCGCCAT ACCACATTTG TAG                                     33

(2) INFORMATION FOR SEQ ID NO:4:
```

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:4:

GCCGCGGCTC TAGAGCCAGA CATGATAAGA TAC                                            33

(2) INFORMATION FOR SEQ ID NO:5:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:5:

AAGCTTGTGC TAGCTATCCC GCCCCTAACT CCG                                            33

(2) INFORMATION FOR SEQ ID NO:6:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:6:

CGAATTCGGT CGACCGCAAA AGCCTAGGCC TCC                                            33

(2) INFORMATION FOR SEQ ID NO:7:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:7:

GTCTATAGCA TGCTCCCCTG CTCCGACCCG                                                30

(2) INFORMATION FOR SEQ ID NO:8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:8:

GGTACCGAAT TCTCCTGCGG GGAGAAGCAG                                                30

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

CGCCAAGCTT GGCCATTGCA TACGGT                                26

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GAGGTCTAGA CGGTTCACTA AACGAGCTCT                             30

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GAATTCGCTA GCGACAGGAG CCAGATCATG AAATG                       35

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CCATGGCCTG AGGTCATGTG CAACTAACAC CTTGT                       35

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

GAATTCGCAT GCGGCATGGA GGACAAAACT AGAG                        34

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
GAATTCGAGC TCACAGCTCT TGCCAGGCAA GGCA                                            34

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGATCCGCGG CCGCGCCCAC TAGAAACTGA GAAACC                                          36

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GAATTCAGAT CTGGTACCAT GTTTTGCTGG AAGC                                            34

(2) INFORMATION FOR SEQ ID NO:17:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGATCCGAGC TCTTGAGGAG TTTAAGAAGA GAGTT                                           35

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AGCTGCATAT TTTCTGTAGT AATCC                                                      25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CCTGGTGTAG CAGTAGCCAG CACAC                                                      25

(2) INFORMATION FOR SEQ ID NO:20:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:20:

GAATTCGCTA GCCTGCCGCT TCCAGGCGTC                                           30

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GAATTCCCTA AGGCATAACC CCATGGAGGC C                                         31

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GATGATGAAT TCGCCCCCTA GAGCTGGGCC                                            30

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

ATGATGGCGG CCGCCCCTCT CGGGGACACT GG                                        32

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

AGAGAGACGC GTGCCATACC ACATTTGTAG                                            30

(2) INFORMATION FOR SEQ ID NO:25:

(i) SEQUENCE CHARACTERISTICS:
        (A) LENGTH: 28 base pairs
        (B) TYPE: nucleic acid
        (C) STRANDEDNESS: single
        (D) TOPOLOGY: linear -continued

```
    (ii) MOLECULE TYPE: DNA (xi) SEQUENCE DESCRIPTION: SEQ ID NO:25:

GCAGCAGGAT CCAGACATGA TAAGATAC                                28

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GAATTCTCTA GAAAGGTCGT GCTGGCATTC                               30

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CTGGGCAAGG TGGCGTAG                                            18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GAGCGCAAAT GTTGTGTC                                            18

(2) INFORMATION FOR SEQ ID NO:29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GAATTCACGC GTCACGCGAC CCCGAGAGCC                               30

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:
```

AGAGAGGCAT GCTCCCCATC CCATGTATTT                30

(2) INFORMATION FOR SEQ ID NO:31:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:31:

GAATTCGTCG ACCGAGTGCA GATTCCATGT                30

(2) INFORMATION FOR SEQ ID NO:32:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:32:

CTGGGTTGCT GAGTTCCGCA AAGTAGCTGG GTCTGG         36

(2) INFORMATION FOR SEQ ID NO:33:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:33:

CGGGGGTCGG GGCTGTTATC TGCATGTGTG CGTGCG         36

(2) INFORMATION FOR SEQ ID NO:34:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:34:

CGCCAAGCTT GGCCATTGCA TACGTT                    26

(2) INFORMATION FOR SEQ ID NO:35:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:35:

GAGGTCTAGA CGGTTCACTA AACGAGCTCT                30

(2) INFORMATION FOR SEQ ID NO:36:

-continued (i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

GGACGCGTGG ATCCAGACAT GATAAGATA                                                29

(2) INFORMATION FOR SEQ ID NO:37:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:37:

GGACGCGTCA GCTGTGGAAT GTGTGTCAG                                                29

(2) INFORMATION FOR SEQ ID NO:38:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:38:

AAGCAGAGCT CGTTTAGTGA ACCG                                                     24

(2) INFORMATION FOR SEQ ID NO:39:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:39:

TGAGCGTGAG TTCTGTGGAA TGTG                                                     24

(2) INFORMATION FOR SEQ ID NO:40:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:40:

TGAGCGTGAG TTCTGTGGAA TGTG                                                     24

GENE MANIPULATION AND EXPRESSION USING GENOMIC ELEMENTS

CROSS-REFERENCE TO RELATED APPLICATIONS

This application is a continuation of application Ser. No. 08/102,567 filed Aug. 5, 1993 (U.S. Pat. No. 5,578,461), which is a continuation of Ser. No. 08/001,898 filed Jan. 7, 1993 (abandoned), which is a continuation of Ser. No. 07/696,216 filed May 6, 1991 (abandoned) which is a continuation-in-part of application Ser. No. 07/432,069 filed Nov. 6, 1989 (abandoned), and claims priority to PCT/US90/06425 filed Nov. 6, 1990.

TECHNICAL FIELD

The field of this invention concerns the manipulation and expression of mammalian genes.

BACKGROUND

With the development of genetic engineering over the last two decades, including restriction enzymes, reverse transcriptase, cloning, polymerase chain reaction, sequencing, and monoclonal antibodies, there has been an extraordinary increase in the ability to isolate, identify and manipulate nucleic acid sequences. As a result of these capabilities, numerous genes and their transcriptional control elements have been identified and manipulated. The genes have been used for producing large amounts of a desired protein in heterologous hosts (bacterial and eukaryotic host cell systems).

In many cases, the process of obtaining coding sequences and eliciting their expression has been a long and arduous one. The identification of the coding sequence, either cDNA or genomic DNA, has frequently involved the construction of libraries, identification of fragments of the open reading frame, examining the flanking sequence, and the like. In mammalian genes where introns are frequently encountered, in many instances, the coding region has been only a small fraction of the total nucleic acid associated with the gene. In other cases, pseudogenes or multi-membered gene families have obscured the ability to isolate a particular gene of interest. Nevertheless, as techniques have improved, there has been a continuous parade of successful identifications and isolation of genes of interest.

For many reasons, it may be desirable to manipulate the coding region or the transcriptional regulatory regions without isolating the coding region or cloning the coding region on a fragment where the coding region is the primary sequence. These reasons may includes ease of manipulation, development of different pathways for expression, or the like.

Also, in many situations, one is primarily interested in a source of the protein product. The cell type in the body which produces the product is frequently an inadequate source. There is, therefore, significant interest in developing alternative techniques for producing proteins of interest in culture, with cells which provide for economic and efficient production of the desired protein and, when possible, appropriate processing of the protein product.

Relevant Literature

Mansour et al., *Nature,* 336:348–352 (1988), describe a general strategy for targeting mutations to non-selectable genes. Weidle et al., *Gene,* 66:193–203, (1988), describe amplification of tissue-type plasminogen activator with a DHFR gene and loss of amplification in the absence of selective pressure. Murnane and Yezzi, *Somatic Cell and Molecular Genetics,* 14:273–286, (1988), describe transformation of a human cell line with an integrated selectable gene marker lacking a transcriptional promoter, with tandem duplication and amplification of the gene marker. Thomas and Capecchi, *Cell,* 51:503–512, (19871, describe site-directed mutagenesis by gene targeting in mouse embryo-derived stem cells. Song et al., *Proc. Natl. Acad. Sci. USA,* 84:6820–6824, (1987), describe homologous recombination in human cells by a two staged integration. Liskay et al., "Homologous Recombination Between Repeated Chromosomal Sequences in Mouse Cells," Cold Spring Harbor, *Symp. Quant. Biol.* 49:13–189, (1984), describe integration of two different mutations of the same gene and homologous recombination between the mutant genes. Rubnitz and Subramani, *Mol. and Cell. Biol.* 4:2253–2258, (1984), describe the minimum amount of homology required for homologous recombination in mammalian cells. Kim and Smithies, *Nucl. Acids. Res.* 16:8887–8903, (1988), describe an assay for homologous recombination using the polymerase chain reaction.

Burke, et al., *Science* 236:806–812 (1987) describe yeast artificial chromosomes (YACs). See also, Garza, et al., *Science* 246:641–646 (1989) and Brownstein, et al. *Science* 244:1348–1351 (1989).

See also, U.S. application Ser. No. 432,069, filed Nov. 6, 1989 and Ser. Nos. 466,088, filed Jan. 12, 1990 and 610,515, filed Nov. 11, 1990, which applications are incorporated herein by reference.

SUMMARY OF THE INVENTION

Expression of mammalian proteins is achieved by homologous recombination, where a DNA sequence is integrated into the genome or large fragment thereof for enhancing the expression of the target gene. The modified sequence may then be transferred to a secondary host for expression. Where an amplifiable gene is integrated adjacent to the target gene, the target region may be amplified for enhanced expression.

Two different targets may be employed: homologous recombination in a host cell comprising the wild type target gene; or integration into a selected YAC(s) or YAC library and transfer of the target region to the expression host. When using a YAC or YAC genomic library containing mammalian DNA, particularly human, the gene of interest is manipulated by homologous recombination, which includes the introduction of an amplifiable gene in proximity to the target gene to allow for amplification, and may in addition include, depending upon the expression host, modification of the transcriptional system, and modification(s) of the coding region. Depending upon whether the gene can be expressed in the yeast host, usually the YAC will be transformed into a mammalian cell expression host for integration and expression of the target gene. Amplification can now be induced and cells selected for stable high levels of expression of the target protein.

DESCRIPTION OF THE SPECIFIC EMBODIMENTS

Methods and compositions are provided for production of mammalian proteins of interest in culture, particularly where one wishes to manipulate the native transcriptional system and/or coding region. The method employs integrating DNA by homologous recombination into genomic DNA, either in the native primary host cell or in a yeast primary host cell, using YAC(s) or YAC genomic library as the source of the target gene. The former technique is described in Patent application Ser. No. 432,069, filed Nov. 6, 1989 (now abandoned).

For transformation of the primary host cell, the cells may be grown and transformed with the DNA targeting construct, using any of a variety of selection techniques for selecting cells having the proper integration. Usually, there will be only one or two integration steps. For the most part, the constructs and techniques employed will be the same for targeting a gene in a chromosome of a native cell or targeting a gene in a large genomic fragment in a YAC.

The YAC library is maintained and propagated in a yeast host and homologous recombination is then employed for integrating a DNA targeting construct, usually comprising an amplifiable gene for integration into a target region comprising the target gene, which target gene encodes the protein of interest, while also allowing for, in the same or separate step, manipulation of the transcriptional system and/or the coding region. The modified yeast cells may then be analyzed and sequences providing for the desired modifications identified. The amplifiable region may then, as appropriate, be transformed into the expression host and the amplifiable region amplified.

"Transform" includes transform, transfect, transduce, conjugate, fuse, electroporate or any other technique for introducing DNA into a viable cell.

After amplification, by employing the amplifiable gene, the transformed hosts are then screened for production of the target protein and stability and derivative cell lines are selected for desired levels of production, which cells may be expanded and used for production of the desired protein in culture.

The source of the DNA, as the primary cell or DNA in the YAC, may be any mammalian cell of interest, particularly mammalian cells which do not grow readily in culture, more particularly primate cells, especially human cells, where the human cells may be normal cells, including embryonic, or neoplastic cells, particularly normal cells. Various cell types may be employed as the primary cells, including fibroblasts, particularly diploid skin fibroblasts, keratinocytes, myoblasts, lymphocytes, glia, epithelial cells, neurons, endothelial cells, or other somatic cells, or germ cells. Of particular interest are skin fibroblasts, which can be readily propagated to provide for large numbers of normal cells, embryonic kidney cells, and the like. These cells may or may not be expressing the gene of interest. In those instances where the target gene is inducible or only expressed in certain differentiated cells, one may select cells in which the target gene is expressed, which may require immortalized cells capable of growth in culture.

A number of amplifiable genes exist, where by appropriate use of a selection agent, a gene integrated in the genome will be amplified with adjacent flanking DNA. Amplifiable genes include dihydrofolate reductase (DHFR), metallothionein-I and -II, preferably primate metallothionein genes, adenosine deaminase, ornithine decarboxylase, glutamate synthase, etc. The amplifiable gene will have transcriptional signals which are functional in the secondary or expression host and may be functional in the primary host, particularly where amplification is employed in the primary host or the amplifiable gene is used as a marker.

The target genes may be any gene of interest, there already having been a large number of proteins of interest identified and isolated with continual additions to the list. Proteins of interest include cytokines, such as interleukins 1–11; growth factors such as EGF, FGF, PDGF, and TGF somatotropins; growth hormones; or other hormones, such as FSH, LH, etc.; colony stimulating factors, such as G-, M-, and GM-CSF; erythropoietin; steel factor; receptor antagonists, such as IL-1rA; plasminogen activators, such as tissue and urine; enzymes, such as superoxide dismutase; interferon $-\alpha$, $-\beta$, $-\gamma$ or modifications thereof; T-cell receptors; surface membrane proteins; insulin; lipoproteins; $\alpha$1-antitrypsin; CD proteins, such as CD3, 4, 8, 19; clotting factors, e.g., Factor VIIIc, IX, and von Willebrands factor; anticlotting factors, such as Protein C; atrial naturetic factor, tumor necrosis factor; transport proteins; homing receptors; addressins; regulatory proteins; etc.

The YACs are prepared in accordance with conventional ways. Genomic DNA is cleaved enzymatically, mechanically, or by other means to provide fragments which will usually have at least about 50 kbp, more usually at least about 100 kbp, conveniently at least about 200 kbp and usually not more than about 2,000 kbp, more usually not more than about 1,000 kbp. The genomic DNA is inserted into a YAC and then screened using appropriate probes for identifying the presence of the target gene. The presence of the YAC may be verified by a selective medium for the markers present on the YAC. Yeast cells containing a YAC or YAC library may be characterized by hybridization analyses or by the polymerase chain reaction (PCR) using primers. The identified YAC(S) may then be used for manipulation.

The YAC will normally be transferred from the original yeast host to a different yeast host which is convenient for manipulation. The new host will be a haploid or diploid strain having a plurality, usually at least 2, and may have 5 or more mutations in different genes which allow for selection by complementation. Total yeast. DNA from the original yeast host may be transformed into yeast cells or spheroplasts yielding cells, which may serve as the hosts for the manipulations. The resulting transformants may be plated on selective media which selects against transformants lacking the complementation markers present on the YAC.

Alternatively, one may transfer the YAC by a genetic cross. The recipient host for manipulation will normally be either a haploid or diploid host having a genetic defect which will be complemented by the genotype of the original yeast strain. If diploid, the recipient host is sporulated and ascospores are mixed with the original yeast host on an appropriate medium to allow mating. If a haploid and of opposite mating type to the original host strain, cells may be mated directly. Hybrid diploids are selected on selective media, where only cross-hybrids grow due to complementation between the non-allelic auxotrophic markers. Hybrids may then be sporulated and either random spores selected, for example, using expression of the heterozygous recessive drug-resistance marker, can1, to select for haploid meiotic products, or tetrads dissected using a micromanipulator. The meiotic products may then be analyzed genetically for the presence of the YAC markers, as well as the genetic markers present in the recipient strain. The presence of the YAC may be confirmed by hybridization or PCR analyses.

The manipulation of the mammalian DNA sequence in the YAC may be achieved in accordance with known techniques for homologous recombination in yeast. Thus, the sequence to be integrated into the mammalian sequence will have a region of homology of at least about 50 bp, more usually at least about 200 bp, usually at least about 50 bp at one terminus of the sequence homologous with the recombination target region, more usually at least about 200 bp, and usually at least 5 bp at the other terminus. The greater homology will usually be at the 5'- terminus for the gene activation or 3' terminus for generating other modifications, such as protein fusions or modifications aimed at increasing mRNA stability. Preferably, there will be at least a total of 100 bp of homologous sequence, more preferably at least about 200 bp with at least about 50 bp at each terminus. The homologous sequence may be 1 kbp or more.

Various sequences having homology to the target region may be employed. In addition to using sequences unique to the target region one may also use sequences which are homologous to repetitive sequences found in the mammalian genome, such as the Alu, LINE, THE, etc. sequence, where on the targeting construct such sequence may be present in one or multiple copies, usually not more than about 10 copies. Alternatively, one may utilize sequences from a YAC arm, such as prokaryotic sequences associated with the YAC arm, genetic markers on the YAC which are absent from the yeast genome, or the like. Where homologous vector arm sequences are employed, one or more kb of homology may be used.

The use of these alternative sequences is particularly helpful when only a small amount of 5'-untranslated region or N-terminal amino acid sequence about the target gene information is known. The 3'-terminus will generally have at least about 20 bp of homology.

Alternatively, one may have one region of homology followed by other sequences to be inserted and a telomere as the construct, (referred to as a half-YAC) where a centromere may or may not be present.

The sequence to be integrated into the mammalian sequence may be introduced into the primary host by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin in resistance etc., or an auxotrophy marker (HIS3, TRP1, LEU2, URA3, ADE2, LYS2, etc.) for use in yeast cells.

Depending upon the nature of the modification and associated targeting construct, various techniques may be employed for identifying targeted integration, Conveniently, the DNA may be digested with one or more restriction enzymes and the fragments probed with an appropriate DNA fragment which will identify the properly sized restriction fragment associated with integration.

Besides an amplifiable gene, other DNA sequences may be employed to enhance expression, either by themselves or in combination with the amplifiable gene. Thus, one may use different promoter sequences, enhancer sequences, or other sequence which will allow for enhanced levels of expression in the expression host. Thus, one may combine an enhancer from one source, a promoter region from another source, a 5'-noncoding region upstream from the initiation methionine from the same or different source as the other sequences, and the like. One may provide for an intron in the non-coding region with appropriate splice sites or for an alternative 3'-untranslated sequence or polyadenylation site. Depending upon the particular purpose of the modification, any of these sequences may be introduced, as desired.

Other modifications may also be included. With relatively small deletions, insertions, point mutations, and the like, where relatively small intends under 1 kbp, usually under 500 bp, the flanking region may include such modification, where desirably at least about 50 bp of homologous sequence is at the terminus. Thus, modifications may include introduction of an enhancer sequence, introduction or substitution of or removal of a signal leader, removal of a splice donor or accceptor or an intron modification thereof, changes in the coding sequence, such as deletions, insertions, or substitutions, where the substitution provides for a change in the amino acid, or combinations thereof. Where two non-contiguous mutations are to be introduced, depending upon the nature and site of the mutations, one may wish to provide for the mutations in two steps, where either of the two steps may be carried out first.

A wide variety of mutations may be of interest, not only as to modifications in the coding sequence, but also in the preparation of fusion proteins where, the target gene may be retained intact or a portion of the target gene may be substituted with the integrating sequence. A number of fusion proteins have found interest, where a constant region from a member of the immunoglobulin superfamily, particularly antibodies, more particularly A IgG isotype, may be fused to the target protein. Alternatively, one may wish to introduce an enzyme, metallothionein, homing receptor, glycoside recognition site, phospholipid recognition site, or the like. In this manner, one may modify the target protein to provide for desirable characteristics which are not naturally present with the target protein.

In carrying out one or multiple transformation steps, each step may be carried out in substantially the same way, except that one may choose to use various techniques other than selection at one or both steps. Where selection is intended, the sequence to be integrated will have with it a marker gene, which allows for selection. The marker gene may conveniently be downstream from the target gene and may include resistance to a cytotoxic agent, e.g. antibiotics, heavy metals, or the like, resistance or susceptibility to HAT, gancyclovir, etc., complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

Yeast are particularly susceptible to homologous recombination, with a high degree of efficiency. Thus, the subject methodology allows for modification of the target locus with a high success rate so that one or a plurality of homologous recombinations may be carried out to achieve any particular modeling of the transcriptional initiation system, the coding region, or other aspect of the sequence of interest, as well as introduction of other sequences in cis, e.g., amplifiable genes.

For homologous recombination, constructs will be prepared where the amplifiable gene will be flanked, normally on both sides with DNA homologous with the DNA of the target region. Depending upon the nature of the integrating DNA and the purpose of the integration, the homologous DNA will.generally be within 100 kb, usually 50 kb, preferably about 25 kb, of the transcribed region of the target gene, more preferably within 2 kb of the target gene. Where modeling of the gene is intended, homology will usually be present proximal to the site of the mutation. By gene is intended the coding region and those sequences required for transcription of a mature mRNA. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

In the case of the amplifiable gene, the homologous sequence will be joined to the amplifiable gene, proximally or distally. Usually a sequence other than the wild-type sequence normally associated with the target gene will be used to separate the homologous sequence from the amplifiable gene on at least one side of the amplifiable gene. Some portion of the sequence may be the 5' or 3' sequence associated with the amplifiable gene, as a result of the manipulations associated with the amplifiable gene.

The integrating constructs may be prepared in accordance with conventional ways, where sequences may be synthesized, isolated from natural sources, manipulated, cloned,. ligated, subjected to in vitro mutagenesis, primer repair, or the like. At various stages, the joined sequences may be cloned, and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., $E.$ $coli,$ and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host or yeast containing YAC.

In the case of the primary mammalian host, a replicating vector may be used. Usually, such vector will have a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium; the gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the targeting construct by means of the selectable marker. Where the selectable marker is not present, one may select for the presence of the construct by the amplifiable gene. For the neo gene or the herpes tk gene, one could employ a medium for growth of the transformants of about 0.1–1 mg/ml of G418 or may use HAT medium, respectively. Where DHFR is the amplifiable gene, the selective medium may include from about 0.01–0.5 $\mu$M of methotrexate or be deficient in glycine-hypoxanthine-thymidine and have dialysed serum (GHT media).

In carrying out the homologous recombination, the DNA will be introduced into the expression host. Techniques which may be used include calcium phosphate/DNA co-precipitates, microinjection of DNA into the nucleus, electroporation, yeast protoplast fusion with intact cells, transfection, polycations, e.g., polybrene, polyornithine, .etc., or the like. The DNA may be single or double stranded DNA, linear or circular. For various techniques for transforming mammalian cells, see Keown et al., *Methods in Enzymology* (1989)., Keown et al., *Methods and Enzymology* (1990) Vol. 185, pp. 527–537 and Mansour et al., *Nature,* 336:348–352, (1988).

Upstream and/or downstream from the target region construct may be a gene which provides for identification of whether a double crossover has occurred. For this purpose, the herpes simplex virus thymidine kinase gene may be employed since the presence of the thymidine kinase gene may be detected by the use of nucleoside analogs, such as acyclovir or gancyclovir, for their cytotoxic effects on cells that contain or lack a functional HSV-tk gene. The absence of sensitivity to these nucleoside analogs indicates the absence of the thymidine kinase and, therefore, where homologous recombination has occurred, that a double crossover event has also occurred.

Once the target region has been modified and the presence of the appropriate modifications established using restriction analysis, sequencing, hybridization, PCR etc., the manipulated YAC may then be used directly or may be further manipulated to reduce its size, e.g., restriction digestion or targeted fragmentation with.a repeated mammalian sequences.

It may be desirable to increase the number of copies of the YAC per yeast cell in order to increase the efficiency of the transfer into mammalian cells. One may use a YAC with its appropriate host strain that allows a multi-fold amplification of the YAC. See, for example, Smith et al., PNAS (1990) 87:8242–8246. The YAC may be manipulated, as appropriate, to provide for appropriate markers for introduction of the construct into the amplifiable YAC. The amplifiable YAC, when amplified, may also find use to improve the efficiency of gene targeting and homologous recombination.

Various secondary mammalian expression hosts are available and may be employed. These hosts include CHO cells, particularly DHFR deficient cells, monkey kidney cells, C127 mouse fibroblasts, 3T3 mouse cells, Vero..cells, etc. In the case of amplification, desirably the hosts will have a negative background for the amplifiable gene or an amplifiable gene which is substantially less responsive to the amplifying agent.

In the presence of a marker, the transformed cells are grown in selective medium containing, for the DHFR gene about 0.01–0.5 $\mu$M methotrexate or GHT media with dialyzed serum and, where another marker is present, e.g., the neo gene, the medium may contain from about 0.1–1 mg/ml G418. The resistant colonies are isolated and may then be analyzed for the presence of the construct in juxtaposition to the target gene. This may be as a result of detection of expression of the target gene product, where there will normally be a negative background for the target gene product, use of PCR, Southern hybridization, or the like.

The cells containing the amplifying construct are then expanded and subjected to selection and amplification with media containing progressively higher concentrations of the amplifying reagent, for example, 0.1–200 µM of methotrexate for the DHFR gene, and may be analyzed at each selection step for production of the target product. Expansion will include at least duplication and may result in at least 5 copies, preferably 10 copies or more in a tandem relationship. Thus protein production will be increased at least 1.5 fold from expression from a single copy, usually at least 3 fold, preferably at least 5 fold.

The various clones may then be screened for optimum stable production of the target product and these clones may then be expanded and used commercially for production in culture. In this manner, high yields of a product may be obtained, without the necessity of isolating the message and doing the various manipulations associated with genetic engineering or isolating the genomic gene, where very large genes can be a major research and development effort.

The following examples are offered by way of illustration and not by way of limitation.

EXPERIMENTAL

Activation of FSH-β, gene expression

Construction of a FSH-β, gene targeting vector: To activate the expression of the FSH-p gene, a YAC targeting vector (pYFT1) is constructed containing the following elements (5' to 3'): a 5' targeting region consisting of nucleotides −452 to −36 of the FSH-β gene (Jameson et al. *Mol. Endocrinology.* (1988) 2:806–815), an FSH-α CDNA expression cassette, a dihydrofolate reductase (DHFR) expression cassette, the yeast selectable marker LEU2, the human cytomegalovirus immediate early (CMV IE) region enhancer/promoter/splice donor sequences, and a 3' targeting region consisting of nucleotides +100 to +850 of the FSH-β, gene. This plasmid. is derived from the plasmids pTD-F and pMF-F. pTD-F is constructed by three successive fragment insertions into pTD, which is created by inserting the synthetic polylinker 5'-Bsu36I-KpnI-MluI-XhoI-Bsu36I-3' into PSKII (Stratagene) between the KpnI and SacI sites, with the loss of those sites. First, the 1.95 kb PvuII/BamHI fragment of SV2DHFR (Subramani et al. *Mol. Cell. Biol.* (1981) 1:854–864) encoding the SV40 early promoter, the DHFR gene, the SV40 t antigen intron and the SV40 early polyadenylation site is joined to MluI linkers and cloned into the MluI site. Second, the 2.0 kb BssHII fragment of pIKFSH-α (described below) encoding an FSH-α cDNA expression cassette is joined to KpnI linkers and cloned into the KpnI site. Finally, the 2.2 kb Sal I/Xho I fragment of YEp13 (ATCC 37115) encoding the yeast selectable marker LEU2 is cloned into the XhoI site. The order of the three elements within the Bsu36I cassette is 5'-pIKFSHα-SVDHFR-LEU2-3', each having the same transcriptional orientation.

pIKFSH-α is generated by inserting an FSH-α cDNA between the BglII and ApaI sites of pIK (see below). The cDNA is cloned by reverse transcription of 0.2 µg of total RNA from the cell line CHA/GO K-1 (ATCC HTB 168) primed by pdN$_6$ (Pharmacia/LKB), followed by polymerase chain reaction (PCR) with primers 1 and 2. A CDNA clone is obtained which encodes the complete FSH-α coding sequence (Fiddes and Goodman, *J. Mol. Appl. Gen.* (1981) 1:3–18). pIK is a mammalian expression vector constructed by four successive cassette insertions into pMF2, which is created by inserting the synthetic polylinker 5'-HindIII-SphI-EcoRI-AatII-BglI-XhoI-3' into KpnI and SacI sites of pSKII, with loss of the Kpn I and Sac I sites. First, a BamHI-XbaI fragment containing the SV40 T antigen polyadenylation site (nucleotides 2770 to 2533 of SV40, Reddy et al., *Science* (1978) 200:494–502) and an NheI-SalI fragment containing the SV40 origin of replication (nucleotides 5725 to 5578 of SV40) are inserted by three-part ligation between the BglII and XhoI sites, with the loss of the BglII, BamHI, XbaI, NheI, SalI and XhoI sites. These BamHI-XbaI and NheI-SalI fragments are synthesized by PCR with pSV2neo (Southern and Berg, *J. Mol. Appl. Gen.* (1982) 1:327–341) as the template using oligonucleotide primer pairs 3 and 4, and 5 and 6, respectively, which incorporated BamHI, XbaI, NheI and SalI sites at their respective ends. Second, an SphI-EcoRI fragment containing the splice acceptor of the human α1 globin gene second exon (nucleotides +143 to +251) is inserted between the SphI and EcoRI sites. This SphI-EcoRI fragment is synthesized by PCR with pπSVαHP (Treisman et al., *PNAS* (1983) 80:7428–7432) as the template using oligonucleotide primers 7 and 8, which incorporated SphI and EcoRI sites at their respective ends. Third, the synthetic polylinker 5'-EcoRI-BglII-ApaI-AatII-3' is inserted between the EcoRI and the AatII sites. Fourth, a HindIII-SacI fragment containing the CMV IE enhancer/promoter (nucleotides −674 to −19, Boshart et al., *Cell* (1985) 41:521–530) and a SacI-SphI fragment containing the CMV IE first exon/splice donor (nucleotides −19 to +170) are inserted by three-part ligation between the HindIII and SphI sites. The HindIII-SacI fragment is prepared by PCR with pUCH.CMV (M. Calos, Stanford Univ.) as the template using oligonucleotide primers 9 and 10, which incorporated HindIII and SacI sites at their respective ends. The SacI-SphI fragment is chemically synthesized.

pMF-F is constructed by three successive fragment insertions into pMF, which is created by inserting the synthetic polylinker 5'-NheI-Bsu36I-HindIII-SphI-NotI-3' into pSKII between the KpnI and SacI sites, with the loss of those sites. First, a NheI-Bsu36I fragment containing nucleotides −452 to −36 of the FSH-β gene (5' targeting region) is synthesized by PCR with DNA from the human diploid fibroblast line WI38 (ATCC CCL 75) as the substrate and the oligonucleotide primers 11 and 12 and cloned between the NheI and Bsu36I sites. Second, an SphI-NotI fragment containing nucleotides +100 to +850 of the FSH-β gene (3' targeting region) is synthesized as described above with primers 13 and 14 and cloned between the SphI and NotI sites. Finally, an 840 bp HindIII-SphI cassette isolated from pIK containing the CMV IE enhancer, promoter, first exon and splice donor is cloned between the HindIII and SphI sites.

pYFT1 is constructed by inserting the 6.2 kb Bsu36I fragment of PTD-F into the unique Bsu36I site of pMF-F, with the transcriptional orientation of the elements within the Bsu36I fragment identical to the CMV IE enhancer/promoter in pMF-F.

A second YAC targeting vector (pYFT2) for FSH-β gene activation is constructed by inserting the 6.2 Kb Bsu36I fragment of pTD-F into the unique Bsu36I site of pMF-F2. pMF-F2 is constructed by two successive fragment insertions into pMF. First, the NheI-Bsu36I fragment containing nucleotides −452 to −36 of the FSH-β gene is cloned between the NheI and Bsu36I sites. Second, a 670 bp HindIII-SacI cassette isolated from pIK containing the CMV IE enhancer and promoter, and a SacI-NotI fragment containing nucleotides +1 to +850 of the FSH-β gene (3' targeting region) are inserted by three-part ligation between the HindIII and NotI sites. The SacI-NotI fragment is synthesized by PCR using oligonucleotide primers 13a and 14, which incorporate SacI and NotI sites as their respective ends.

```
Oligonucleotide primers:

Primer 1:    5'-GAATTCAGATCTGCAGTTACTGAGAACTCATAAG-3'      (SEQ ID NO:1)

Primer 2:    5'-GAATTCGGGCCCTGCAGTGGAACAAGCTTAATG-3'       (SEQ ID NO:2)

Primer 3:    5'-GGTCGACCTGGATCCGCCATACCACATTTGTAG-3'       (SEQ ID NO:3)

Primer 4:    5'-GCCGCGGCTCTAGAGCCAGACATGATAAGATAC-3'       (SEQ ID NO:4)

Primer 5:    5'-AAGCTTGTGCTAGCTATCCCGCCCCTAACTCCG-3'       (SEQ ID NO:5)

Primer 6:    5'-CGAATTCGGTCGACCGCAAAAGCCTAGGCCTCC-3'       (SEQ ID NO:6)

Primer 7:    5'-GTCTATAGCATGCTCCCCTGCTCCGACCCG-3'          (SEQ ID NO:7)

Primer 8:    5'-GGTACCGAATTCTCCTGCGGGGAGAAGCAG-3'          (SEQ ID NO:8)

Primer 9:    5'-CGCCAAGCTTGGCCATTGCATACGGT-3'              (SEQ ID NO:9)

Primer 10:   5'-GAGGTCTAGACGGTTCACTAAACGAGCTCT-3'          (SEQ ID NO:10)

Primer 11:   5'-GAATTCGCTAGCGACAGGAGCCAGATCATGAAATG-3'     (SEQ ID NO:11)

Primer 12:   5'-CCATGGCCTGAGGTCATGTGCAACTAACACCTTGT-3'     (SEQ ID NO:12)

Primer 13:   5'-GAATTCGCATGCGGCATGGAGGACAAAACTAGAG-3'      (SEQ ID NO:13)

Primer 13a:  5'-GAATTCGAGCTCACAGCTCTTGCCAGGCAAGGCA-3'      (SEQ ID NO:14)

Primer 14:   5'-GGATCCGCGGCCGCGCCCACTAGAAACTGAGAAACC-3'    (SEQ ID NO:15)

Primer 15:   5'-GAATTCAGATCTGGTACCATGTTTTGCTGGAAGC-3'      (SEQ ID NO:16)

Primer 16:   5'-GGATCCGAGCTCTTGAGGAGTTTAAGAAGAGTT-3'       (SEQ ID NO:17)
```

YAC screening: Two yeast artificial chromosome (YAC) libraries are screened to identify YACs containing the human FSH-β locus. Each YAC library is generated in the haploid *Saccharomyces cerevisiae* host strain AB1380 [MAT a ade2-1 (ochre) lys2-1(ochre) trpl ura3 his5 canl-100 (ochre)] using pYAC4 (Burke et al. *Science* (1987) 236:806–812). The YAC contains two yeast selectable markers, TRP1 and URA3. Thus, the presence of a YAC in strain AB1380 is verified genetically by scoring for the presence of the wildtype TRP1 and URA alleles. The CEPH YAC library-(Albertsen et al. 1990, PNAS 87: 4256–4260), which consists of ~50,000 colonies with an average YAC insert size of 430 kb (~7 haploid genome equivalents), is screened by PCR. A total of 113 pools of DNA, each prepared from ~386 yeast colonies, are screened with FSH-β primers 11 and 12 (see above) which generate a 416 bp fragment. The Washington University YAC library (Brownstein et al., *Science* (1989) 244:1348–1351), which consists of ~60,000 colonies with an average YAC insert size of 250 kb (~5 haploid genome equivalents), is screened by hybridization to filters prepared from pulsed-field gels. The YAC colonies are arrayed in pools of ~386 colonies, chromosomal DNA is prepared from each pool and the DNA is separated on pulsed-field gels. The 416 bp FHS-β PCR product prepared with primers 11 and 12 is used as a hybridization probe. Yeast colony hybridization to filters prepared from individual YAC colonies (Traver, Klapholz, Hyman and Davis 1989; *PNAS* 86:5898–5902) is used to screen for FSH-β-containing YACs from each of the positive pools. Several positive YAC colonies are identified and analyzed-by Southern blot analysis for the presence of characteristic hybridizing EcoRI, BglII, BamHI and NsiI fragments using the 416 bp fragment as probe. One, designated YAC-FSH-β1, having the expected pattern, is chosen for subsequent experimentation.

Transfer of YAC-FSH-β1 to a new host: All yeast genetic manipulations employ standard methodology essentially as described in Sherman, Fink and Hicks (1986, Laboratory Course Manual for Methods in Yeast Genetics). To efficiently carry out homologous targeting of YAC-FSH-β1, the YAC is transferred to a new haploid yeast host strain, YPH252 (MATα ade2–101 (ochre) lys2–801 (amber) ura3–52 trplΔ1 his3Δ200 leu2Δ1) (Sikorski and Hieter 1989, *Genetics* 122:19–27). This host contains nonreverting alleles of ura3, trp1, leu2 and his3; with the latter three being deletion alleles. Total yeast chromosomal DNA is prepared in agarose plugs using standard methodology (McCormick et al., *Technique* (1990) 2:65–71). The agarose plugs are equilibrated in 25 mM NaCl; 10 mM Tris-HCl pH 7.5; 0.75 mM spermidine trihydrochloride; 0.3 mM spermine tetrahydrochloride, melted at 65° C. and used to transform yeast spheroplasts of the strain YPH252 (Burgers and Percival, *Anal. Biochem.* (1987) 163:321–397; McCormick et al., *J. Methods in Cell and Mol. Biol.* (1990) 2:65–71). Transformants are plated on media lacking uracil to select for the presence of the wildtype URA3 marker contained on the YAC. The presence of the YAC is confirmed by the additional presence of the wildtype TRP1 allele.

Gene targeting of the FSH-β locus: The targeting vectors pYFT1 and pYFT2 are digested with NheI and NotI to liberate ~7.3 kb fragments. These fragments are used to transform yeast spheroplasts of the strain YPH252/YAC-FSHβ1. Total yeast genomic DNA from Leu+transformants is subjected to Southern blot analysis and compared with DNA from untransformed cells to detect targeting of the FSH-β locus. DNA is digested with EcoRI, BglII, BamHI or NsiI and probed with a ~800 bp fragment from the second intron of the FSH-β gene lying outside of the targeting vector. This probe is synthesized by PCR with DNA from WI38 cells as the template using oligonucleotide primers 15 and 16. The resulting ~1.4 kb fragment is digested with PstI and SacI to generate the ~800 bp fragment. Correctly targeted colonies display hybridizing fragments consistent with the insertion of the ~7.0 kb corresponding to pIKFSHα, SVDHFR, LEU2 and CMV enhancer and promoter sequences.

Transfer of the targeted FSH-β locus into CHO cells: Total yeast DNA is used to transfect CHO DHFR-DUKX B 1 (Urlaub and Chasin, 1990, PNAS 7:4216–4220) cells essentially as described by Eliceiri et al. for YAC transfer into Mouse L/tk- cells (Eliceiri et al. 1991, PNAS 88:2179–2183), but optimized for the transfection of CHO cells. Genomic DNA is extracted from the pYFTl-targeted YPH252/YAC-FSH-β1 cells and dialyzed against 1 mM EDTA, 10 mM Tris-HCl pH 7.4 for 48 hours. $2 \times 10^5$ CHO DHFR-cells are plated 12 hr prior to transfection on 6 cm dishes in DME/F12 media supplemented with 10% fetal bovine serum, glycine, hypoxanthine and thymidine (nonselective media). For transfection, 150 µl of 2xHeBS (280 mM NaCl, 50 mM Hepes pH7.1, 1.5 $Na_2HPO_4$) is added to 15 µg of yeast genomic DNA in 150 µl of 0.27M $CaCl_2$. The precipitate is allowed to form at room temperature for 25 minutes, added to cells in the absence of media and incubated for 20 minutes at room temperature, then topped off with 3 ml of media and incubated at 37° C. Four hours later, the cells are washed twice with serum-free media, incubated with 15% glycerol in HeBS for 4 minutes at 37° C., washed again in serum-free media followed by growth in nonselective media for 48 hours. The transfected cells are then split 1:20 into selective media in (DME/F12 supplemented with 10% dialyzed fetal bovine serum) and fed every 3 days. Transfected DNA in CHO DHFR+ transformants is amplified by selection in increasing concentrations of methotrexate. YAC containing CHO DHFR+ clones are plated in selective media at $5 \times 10^5$ cells per 10 cm plate and selected at 0.01 µm methotrexate (Kaufman and Sharp, 1982. J. Mol. Biol. 159:601–621). Surviving colonies are pooled, then tested for increased DNA copy number by Southern blot analysis and increased protein production by immunoprecipitation analysis. The amplification protocol is repeated with increasing concentrations of methotrexate from 0.01 µm to 50 µM, with a three to five-fold increased methotrexate concentration at each step.

Analysis of CHO transfectants: Transfected colonies are expanded and characterized for the production of FSH-α and -β MRNA and biologically active heterodimeric FSH. Total RNA is prepared and the level of correctly initiated FSH-α and FSH-β mRNA is assayed by primer extension (Finer et al., 1987) using the following oligonucleotides:

FSH-α: 5'-AGCTGCATATTTTCTGTAGTAATCC (SEQ ID NO:18)

FSH-β: 5'-CCTGGTGTAGCAGTAGCCAGCACAC (SEQ ID NO:19)

RNA expression is indicated by the detection of primer extension products consistent with the addition of the CMV first exon and polylinker sequence of pIK for FSH-α, and the exchange of the FSH-β first exon by the first exon of the CMV IE region.

Heterodimeric FSH is detected by pulse labeling of transfected clones with $^{35}S$-methionine followed by immunoprecipitation of protein collected from the conditioned media and from cell lysates (Keene et al. 1989, JBC 264, 4769–4775). Analysis on native and denaturing polyacrylamide gels reveals a protein product similar to highly purified human FSH. Biological activity of the expressed product is confirmed using the in vitro granulosa cell aromatase bioassay (Jia et. al., J. Clin. Endocrinol. Metab. (1986) 62:1243–1249; Jia et. al., Endocrinology (1986) 119:1570–1577).

Activation of G-CSF analog expression

Construction of G-CSF targeting vectors: To activate the expression of the G-CSF gene, a YAC targeting vector (pYGT1) is constructed containing the following elements (5' to 3'): a 5' targeting region consisting of nucleotides −361 to −69 of the G-CSF gene (Nagata et al., EMBO J. (1986) 5:575–581), a DHFR expression cassette, the yeast selectable marker LEU2, the human CMV IE enhancer/promoter/splice donor, a human α-1 globin gene splice acceptor, and a 3' targeting region consisting of nucleotides −60 to +167 of the G-CSF gene. This plasmid is derived from plasmids pTD-G and pMF-G. Plasmid pTD-G is constructed by two successive fragment insertions into pTD. First, the 1.95 kb PvuII-BamHI fragment of SV2DHFR encoding the SV40 early promoter, the DIIFR gene, the SV40 t antigen intron and the SV40 early polyadenylation site is joined to MluI linkers and cloned into the MluI site. Second, the 2.2 kb SalI-XhoI fragment of YEpl3 encoding the yeast selectable marker LEU2 is cloned into the XhoI site. The order of these elements within the Bsu36I cassette was 5'-SV2DHFR-LEU2-3', both having the same transcriptional orientation.

pMF-G is constructed by the insertion into pMF of three fragments in two steps. First, an NheI-Bsu36I fragment containing nucleotides −361 to 69 of the human G-CSF gene (5' targeting region) is generated by PCR using oligonucleotide primers 17 and 18, and cloned between the NheI and Bsu36I sites. Second, an EcoRI-NotI fragment containing nucleotides −60 to +167 of the G-CSF gene is generated by PCR using oligonucleotide primers 19 and 20. This EcoRI-NotI fragment and a HindIII-EcoRI fragment from pIK containing the CMV IE enhancer/promoter/splice donor and human α-1 globin splice acceptor, are inserted by three-part ligation between the HindIII and NotI sites.

pYGT1 is constructed by inserting the 4.2 kb Bsu36I fragment of pTD-G into the unique Bsu36I site of pMF-G, with the transcriptional orientation of the elements within the Bsu36I fragment identical to the CMV enhancer/promoter in pMF-G.

To create sequences capable of directing the modification of the G-CSF polypeptide, a YAC targeting vector (pYGT2) is constructed containing the following elements (5' to 3' ): a 5' targeting region consisting of nucleotides +1180 to +1480 of the G-CSF gene, an IgG2 heavy chain cDNA encoding the hinge, CH2 and CH3 domains (amino acids 216–478, Kabat et al 1983, Sequences of Proteins of Immunological Interest), an SV40 early polyadenylation site, the yeast selectable marker HIS3, and a 3' targeting region consisting of nucleotides +1496 to +2599 of the G-CSF gene. The 5' targeting sequences and IgG2 cDNA sequences are configured such that upon successful targeting a sequence encoding a hybrid G-CSF-IgG2 protein would be created in which Gln-176 of G-CSF is fused.to Glu-216 of the IgG2 hinge region. pYGT2 is constructed by four successive fragment insertions into pDS, which is created by inserting the synthetic polylinker 5'-XbaI-MluI-BamHI-SphI-SalI-3' into pSKII between the KpnI and SacI sites, with the loss of those sites. First, an MluI-BamHI fragment containing the SV40 early polyadenylation site (nucleotides 2270 to 2533) is generated by PCR with pSV2DHFR as template using oligonucleotide primers 21 and 22 and inserted between the MluI and BamHI sites. Second, the 1.7 kb BamHI fragment of pNN414 encoding the yeast selectable marker HIS3 (Traver et al, *supra*) is cloned into the BamHI site. Third, an XbaI to blunt-ended fragment containing nucleotides +1180 to +1480 of the G-CSF gene, and a blunt-ended to MluI fragment encoding amino acids 216–478 of the IgG2 heavy chain are inserted in a three part ligation between the XbaI and MluI sites. The G-CSF gene fragment is generated by PCR using oligonucleotide primers 23 and 24, and the IgG2 fragment is generated by PCR with a cDNA clone obtained from a human spleen cDNA library (Clontech) as template using oligonucleotide primers 25 and 26. Finally, a 1.1 kb SphI-SalI fragment containing +1496 to +2599 of the G-CSF gene, generated by PCR using oligonucleotide primers 27 and 28 is inserted between the SphI and SalI sites.

using oligonucleotide primers 17 and 18. Correctly targeted colonies display hybridizing fragments consistent with the insertion of the ~4.1 kb corresponding to IgG2, SV40 and HIS3 sequences. Total DNA is prepared from the doubly targeted yeast strain and used to transfect CHO DHFR− cells as described above for the FSH-β gene. Following gene amplification of the transfected G-CSF-IgG2 sequences, CHO colonies are analyzed for expression of the G-CSF analog.

Analysis of YAC transfected CHO clones:

Secreted G-CSF-IgG2 is characterized by labeling transfected clones with $^{35}$S-methionine followed by immunoprecipitation of culture supernatants and cell lysates as described (Capon et al., *Nature* (1989) 337:525–531). Washed immunoprecipitates are eluted and electrophoresed

```
Primer 17:  5'-GAATTCGCTAGCCTGCCGCTTCCAGGCGTC-3'       (SEQ ID NO:20)

Primer 18:  5'-GAATTCCCTAAGGCATAACCCCATGGAGGCC-3'      (SEQ ID NO:21)

Primer 19:  5'-GATGATGAATTCGCCCCCTAGAGCTGGGCC-3'       (SEQ ID NO:22)

Primer 20:  5'-ATGATGGCGGCCGCCCCTCTCGGGGACACTGG-3'    (SEQ ID NO:23)

Primer 21:  5'-AGAGAGACGCGTGCCATACCACATTTGTAG-3'       (SEQ ID NO:24)

Primer 22:  5'-GCAGCAGGATCCAGACATGATAAGATAC-3'         (SEQ ID NO:25)

Primer 23:  5'-GAATTCTCTAGAAAGGTCGTGCTGGCATTC-3'       (SEQ ID NO:26)

Primer 24:  5'-CTGGGCAAGGTGGCGTAG-3'                   (SEQ ID NO:27)

Primer 25:  5'-GAGCGCAAATGTTGTGTC-3'                   (SEQ ID NO:28)

Primer 26:  5'-GAATTCACGCGTCACGCGACCCCGAGAGCC-3'       (SEQ ID NO:29)

Primer 27:  5'-AGAGAGGCATGCTCCCCATCCCATGTATTT-3'       (SEQ ID NO:30)

Primer 28:  5'-GAATTCGTCGACCGAGTGCAGATTCCATGT-3'       (SEQ ID NO:31)
```

Gene targeting of the G-CSF locus:

Identification of a YAC colony containing the human G-CSF locus (YAC-G-CSF-1) using the 1.1 kb SphI-SalI fragment as probe and transfer of the YAC to yeast strain YPH252 are carried out as described above for the FSH-β locus. To activate the expression of a GCS-F-IgG2 hybrid polypeptide, two successive gene targeting events are carried out using the targeting vectors pYGT1 and pYGT2. First, the targeting vector pYGT1 is digested with NheI and NotI to liberate a 4.7 kb fragment. This fragment is used to transform yeast spheroplasts of the strain YPH252/YAC-G-CSF-1. Total yeast genomic DNA from Leu+ transformants is subjected to Southern blot analysis and compared with DNA from untransformed cells to detect targeting of the G-CSF locus. DNA is digested with restriction enzymes and probed with a ~1.1 kb fragment from the 3' untranslated region of the G-CSF gene lying outside the targeted region. This probe is generated by PCR using oligonucleotide primers 27 and 28. Correctly targeted colonies display hybridizing fragments consistent with the insertion of the ~4.7 kb corresponding to SVDHFR, Leu2 and CMV IE sequences. Next, the targeting vector pYGT2 is digested with XbaI and SalI to liberate a ~4.1 kb fragment. This fragment is used to transform yeast spheroplasts of the strain created by the above targeting event. Total yeast genomic DNA from His+ transformants is subjected to Southern blot analysis and--compared with DNA from untransformed cells to detect targeting of the G-CSF locus. DNA is digested with restriction enzymes and probed with a 300 bp fragment from the 5' untranslated region of the G-CSF gene lying outside the newly targeted region. This probe is generated by PCR on polyacrylamide gels under reducing conditions and visualized by autoradiography to reveal the hybrid polypeptide.

The presence of the G-CSF moiety is confirmed by Western blot analysis. Unlabelled supernatants are similarly immunoprecipitated and electrophoresed and the proteins transferred to nitrocellulose filters (Burnette, *Anal. Biochem* (1981) 112:195) The filters are treated with a rabbit polyclonal anti-human-G-CSF antiserum (Genzyme) and the bands visualized by treating with Horseradish peroxidase-conjugated goat antirabbit-IgG antibody (Boehringer Mannheim) followed by staining with 3,3'-diaminobenzidine and $H_2O_2$.

The following example describes the use of a mammalian primary host cell for the target DNA.

Isolation of a Genomic Clone Containing Sequences for Targeting Erythropoietin

A clone was obtained by screening a human placental DNA genomic library (Clontech) in EMBL 3-SP6/T7 using two 36 bp oligonucleotide probes 5'-CTGGGTTGCTGA GTTCCGCAAAGTAGCTGGGTCGG-3' (SEQ ID NO: 32) and 5'-CGGGGGTCGGGGCTGTTATCTGCATGTG TGCGTGCG-3' (SEQ ID NO:33) to the presumed promoter region of human erythropoietin. From this clone two subclones were created in pSP72 (Krieg and Melton (1987) Meth. Enzymol. 155,397–415), one containing a 5 kb BamHI-HindIII fragment from the region upstream to the coding region of EPO (pTD.1) and one containing a 5 kb HindIII-BamHI fragment coding for EPO (pTD.2).

Construction of DNA Fragment for Targeting Erythropoietin

A plasmid pCG.1 was constructed by replacement of the polylinker of pBluescript SK(−) (Stratagene) between the SacI and KpnI sites with a synthetic double stranded 72 base pair DNA fragment (FIG. 1). Referring to FIG. 2, into pCG.1 was cloned between the HindIII and XbaI sites a 678 bp fragment containing the enhancer and promoter of the immediate early gene of human cytomegalovirus (CMV, Boshart et al. (1985) cell 41, 521–530) obtained by a PCR amplification of the plasmid pUCH.CMV (gift of M. Calos, Stanford U.) using the oligonucleotide primers 5'-CGCCAAGCTTGGCCATTGCATACGTT-3' (SEQ ID NO:34) and 5'-GAGGTCTAGACGGTTCACTAAACGAGCTCT-3' (SEQ ID NO:35) in order to engineer HindIII and XbaI sites respectively onto the ends of the resultant fragment. The resultant plasmid pCG.CMV was used for further constructions.

The 620 bp BstEII-XbaI fragment from the pTD.2 was joined by the used of a BstEII-XbaI adapter to pCG.CMV restricted with XbaI to create the plasmid pCG.CMV/EPO, in which the BstEII site of the EPO fragment is next to the promoter end of the CMV fragment. Into pCG.CMV/EPO was cloned successively a 1.94 kb fragment encoding methotrexate resistance from the plasmid pSV2dhfr (Subramani et al. (1981) Mol. Cell. Biol. 1, 854–864) and a 1.15 kb fragment encoding G418 resistance from the plasmid pMClneo polyA (Thomas and Capecchi (1987) Cell 51, 503–512). The neo gene was obtained as an XhoI-SalI fragment and the dhfr gene was obtained by PCR amplification using the primers 5'-GGACGCGTGGATCCAGACATGATAAGATA-3' (SEQ ID NO:36) and 5'-GGACGCGTCAGCTGTGGAATGTGTGTCAG-3' (SEQ ID NO:37) designed to add MluI sites at the ends of the resultant fragment. The neo and dhfr genes were cloned into the XhoI and MluI sites respectively of pCG.CMV/EPO to give the plasmids pCG.CMV/EPO/DHFR and pCG.CMV/EPO/Neo/DHFR such that their transcription is in the same orientation as that of CMV. Finally, the 5 kb BamHI-HindIII fragment from pTD.1 was added via ClaI adapters at the ClaI site of pCG.CMV/EPO/Neo/DHFR to give pCG.HR1. In pCG.HR1, the 5' 5 kb EPO fragment is in the same orientation as that of the 620 bp BstEII-XbaI fragment with respect to the original lambda clone.

A 9.54 kb fragment containing the 5' 5 kb BamHI-HindIII EPO fragment, the dhfr and G418 markers, the CMV enhancer/promoter and the 620 bp BstEII-XbaI EPO fragment can be released.from pCG.HR1 as a NotI or SacII fragment. This NotI fragment can be used for homologous recombination as it is designed to serve as an omega structure in recombination having 5 kb and 620 bp of homology to facilitate the event (FIG. 3).

For electroporation, the DNA was first cut with NotI, then extracted with phenol/chloroform and precipitated by the addition of ethanol before centrifugation. The resultant DNA pellet was resuspended at a concentration of 2 mg/ml in a volume (10 μl) of 10 mM Tris-Hcl, 1 mM EDTA (TE).

Introduction of DNA into cells

Transformed primary human 293 embryonal kidney cells (ATCC CRL 1573) were cultured in Cellgro DMEM H16 (Mediatech) supplemented with 10% calf serum, glutamine (2 mM) and penicillin (100 U/ml)/streptomycin (0.1 mg/ml) and grown at 37° C. in 5% $CO_2$. At 90% confluency, cells were prepared for electroporation by trypsinization, concentration by brief centrifugation and resuspension in PBS at $10^7$ cells/0.8 ml. The cells were equilibrated at 4° C., and DNA (50 μg) restricted with NotI (as described above) was added. The mixture was electroporated at 960 μF and 260 V with a BioRad Gene Pulser and then iced again for 10 min before plating onto a 10 cm dish. After incubation at 37° C. for 48 hr, the cells from a 10 cm dish were split equally among 5 24-well plates in media containing G418 at 0.6 mg/ml (effective concentration). Under these electroporation conditions, 4–10 colonies/well survive drug selection after 2 weeks.

Detection of Homologous Recombination by PCR Analysis

Using NotI restricted DNA from pCG.HR1, successful homologous recombination is obtained by insertion of the 3.8 kb construct at the targeted EPO locus while simultaneously deleting 1.2 kb of genomic sequence (FIG. 3). PCR is used to detect unique targeting events versus random integration of the DNA as diagrammed in FIG. 4. Two primers are synthesized, one to the 3' end of CMV and the other to the region 3' to the XbaI site used for the 620 bp BstEII-XbaI fragment in the targeting DNA. A homologous recombination event generates a DNA target in the genome from which these primers produce an amplification product of 860 bp.

In order to detect the targeting event, pools of clones (from the electroporated 293 cells) from 4 wells each (representing about 16 colonies) were generated by trypsinizing wells and using 90% of each well for the pool. The remaining 10% of each well was then reseeded back into the well. Genomic DDNA was then prepared from each pool as follows. The cells in each pool were pelleted by centrifugation for 2 min. in a 1.5 ml microcentrifuge tube, resuspended in OBS (20 μl), and treated for 1 hr at 37° C. with a solution (400 μl) containing 10 mM Tris-HCl (pH7.5), 100 mM NaCl, 5 mM EDTA, 1% SDS and RNase A (40 μg/ml). Proteinase K (10 μl, 10 g/ml) was then added, and the samples were incubated for 4 hr at 50° C. before extractions by vigorous vortexing with phenol/chloroform (200 μl each), then with chloroform (400 μl), the addition of ethanol (800 μl each), and centrifugation at 25° C. for 10 min. The DNA pellets were washed with 70% ethanol, dried and resuspended in TE (20 μl). An average of 40 μg of genomic DNA was obtained from each sample.

Approximately 1 μg from each sample of genomic DNA was used for PCR analysis. The DNA in a volume (10 μl) of TE was boiled for 10 min. prior to the addition of PCR mix (40 μl). The reaction (50 μl) contained 10 mM Tris-HCl (pH 9.0 at 25° C.), 50 mM KCl, 1.5 mM $MgCl_2$, 0.01% gelatin, 0.1% Triton X-100, 200 μM dNTPs, 1 μM each of the primers 5'-AAGCAGAGCTCGTTTAGTGAACCG-3' (SEQ ID NO:38) and 5'-TGAGCGTGAGTTCTGTGGAATGTG-3' (SEQ ID NO:39) and 5'-TGAGCGTGAGTTCTGTGGAATGTG-3' , (SEQ ID NO:40) and 1.5 U of Taq DNA polymerase (Promega). Following an initial incubation of 94° C. for 3 min., the samples were subjected to 45 cycles of denaturation at 94° C. for 1 min., annealing at 66° C. for 1.5 min. and extension at 72° C. for 2 min. At the end of the 45 cycles, the samples were incubated an additional 5 min. at 72° C. A portion (20 μl) of each sample was analyzed on a 1% agarose gel run in TBE and stained with ethidium bromide. Out of the 90 pools analyzed from 3 electroporations, two samples were identified which exhibited the correct size fragment by ethidium bromide staining. The DNA from the PCR reaction was recovered and subjected to restriction mapping with XbaI. The correct amplification product should upon treatment with XbaI yield two fragments, 669 bp and 191 bp. The samples from the two pools both yield fragments of the correct sizes. In addition, the sample from pool 1 exhibits other bands in the uncut material.

Following the procedure described previously, metaphase chromosomes are prepared from the recipients demonstrating homologous recombination with DHFR and transformed in DHFR deficient CHO cells. After isolating resistant colonies and analyzing for expression of EPO, the cell clones are grown in selective medium containing progressively higher concentrations of methotrexate (0.02–80 μM) with steps of 4-fold increases in concentration. The cells are then harvested, cloned and screened for production of EPO. Clones providing for at least 2-fold enhancement of EPO production are isolated.

It is evident from the above results, that a simple accurate technique has been developed which allows for the ready manipulation of genes with high efficiency, introduction of amplifiable markers to allow for amplification of a target gene, modifications of genes, and transfer of the resulting modified chromosomal DNA to a mammalian expression host; to provide for efficient expression of the desired product having the same, substantially the same, or different composition from the natural product. Thus, one can obtain processing, combinations of products due to variation in splicing, processing, such as glycosylation, acetylation, methylation, or the like, as well as high and efficient levels of stable production of the desired product. Thus, a rapid, efficient methodology is.provided for producing expression constructs for transformation into mammalian expression hosts, without the need for isolating and purifying the target gene and allowing for modification of the target gene with high efficiency.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto departing from the spirit or scope of the appended claims.

What is claimed is:

1. A yeast artificial chromosome comprising mammalian DNA that includes a mammalian target gene, wherein a nucleotide regulatory sequence, heterologous to the mammalian target gene, is in operable association with the mammalian target gene such that the nucleotide regulatory sequence directs expression of the mammalian target gene when the yeast artificial chromosome is present in a mammalian cell.

2. The yeast artificial chromosome of claim 1 in which the yeast artificial chromosome further contains an amplifiable gene operably associated with the mammalian gene.

3. The yeast artificial chromosome of claim 1 or 2 in which the mammalian gene is a human gene.

4. The yeast artificial chromosome of claim 1 or 2 in which the heterologous regulatory sequence is a viral promoter or a promoter/enhancer.

5. The yeast artificial chromosome of claim 4 in which the promoter/enhancer is a cytomegalovirus promoter/enhancer.

6. The yeast artificial chromosome of claim 2 in which the amplifiable gene is dihydrofolate reductase, metallothionein-I, metallothionein-II, adenosine deaminase, ornithine decarboxylase, or glutamine synthetase.

7. The yeast artificial chromosome of claim 1 or 2 in which the mammalian gene further contains a mutation located in an amino acid coding region, an intron, a 5'-untranslated region, or a 3'-untranslated region.

8. A yeast host containing the yeast artificial chromosome of claim 1.

9. A yeast host containing the yeast artificial chromosome of claim 2.

10. A yeast host containing the yeast artificial chromosome of claim 3.

11. A yeast host containing the yeast artificial chromosome of claim 4.

12. A yeast host containing the yeast artificial chromosome of claim 5.

13. A yeast host containing the yeast artificial chromosome of claim 6.

14. A yeast host containing the yeast artificial chromosome of claim 7.

15. A mammalian continuous cell line transformed with the yeast artificial chromosome of claim 1, or progeny of the transformed cell line, that express the mammalian gene controlled by the heterologous nucleotide regulatory sequence.

16. A mammalian continuous cell line transformed with the yeast artificial chromosome of claim 2, or progeny of the transformed cell line, that express the mammalian gene controlled by the heterologous nucleotide regulatory sequence, which mammalian gene is amplified under conditions that amplify the amplifiable gene.

17. The mammalian continuous cell line of claim 15 or 16 in which the mammalian gene is a human gene.

18. The mammalian continuous cell line of claim 15 or 16 in which the heterologous regulatory sequence is a viral promoter or a promoter/enhancer.

19. The mammalian continuous cell line of claim 18 in which the promoter/enhancer is a cytomegalovirus promoter/enhancer.

20. The mammalian continuous cell line of claim 16 in which the amplifiable gene is dihydrofolate reductase, metallothionein-I, metallothionein-II, adenosine deaminase, ornithine decarboxylase, or glutamine synthetase.

21. The mammalian continuous cell line of claim 15 or 16 in which the mammalian gene further contains a mutation located in a amino acid coding region, an intron, a 5'-untranslated region, or a 3'-untranslated region.

* * * * *